US005763206A

United States Patent [19]
Hammerstedt et al.

[11] Patent Number: 5,763,206
[45] Date of Patent: Jun. 9, 1998

[54] PROCESS FOR EVALUATING FERTILITY OF SPERMATOZOA SAMPLES

[75] Inventors: Roy H. Hammerstedt, Boalsburg; Guy F. Barbato; Palmer G. Cramer, both of State College, all of Pa.

[73] Assignee: The Penn State Research Foundation, University Park, Pa.

[21] Appl. No.: 600,417

[22] Filed: Feb. 13, 1996

Related U.S. Application Data

[63] Continuation of Ser. No. 234,448, Apr. 28, 1994, abandoned.
[51] Int. Cl.$^6$ .................. C12Q 1/02; A61K 35/54
[52] U.S. Cl. .................. 435/29; 435/806; 424/561; 424/581
[58] Field of Search .................. 435/29, 284.1, 435/287.1, 287.9, 288.7, 806; 424/561, 581, 582; 514/2

[56] References Cited

PUBLICATIONS

Alexander A., Effects of Genotype and Cryopreservation of Avian Semen on Fertility and Number of Perivitelline Spermatozoa, British Poultry Science 34: 757–764, 1993.

Wishart G., Regulation of the Length of the Fertile Period in the Domestic Fowl by Numbers of Oviducal Spermatozoa, as Relflected by Those Trapped in Laid Eggs, J Reproduc Fert 80: 493–498, 1987.

Cooper "The Tools of Biochemistry" pp. 355–363 John Wiley & Sons, 1977.

Wishart J Reprod Fert. (1987) 80:493–498.

Amann, R.P., "Can the Fertility Potential of a Seminal Sample be Predicted Accurately?", J. Androl., vol. 10, pp. 89–98 (1989).

Amann, R.P. and Hammerstedt, R.H., "In Vitro Evaluation of Sperm Quality: An Opinion", J. Androl., vol. 14, pp. 397–406 (1993).

Anonymous, WHO Laboratory Manual for the Examination of Human Semen and Sperm–cervical Mucus Interaction, 3d Ed., pp. 1–2, 23–27, 43–44, & 82–86, Cambridge University Press, Cambridge (1992).

Bakst, M.R. and Howarth, Jr., B., "Hydrolysis of the Hen's Perivitelline Layer by Cock Sperm in vitro", Biol. Reprod., vol. 17, pp. 370–379 (1977).

Bavister, B.D., Cummins, J. and Roldan, E.R.S., Fertilization In Mammals, Serono Symposia U.S.A., pp. 65–75, 169–177, & 239–266, Norwell (1990).

Bleil, J.D. and Wassarman, P.M., "Mammaliam Sperm–Egg Interaction: Identification of a Glycoprotein in Mouse Egg Zonae Pellucidaw Possessing Receptor Actvity for Sperm", Cell., vol. 20, pp. 873–882 (1980).

Bramwell, R.K. and Howarth, B., "Preferential Attachment of Cock Spermatozoa to the Perivitelline Layer Directly Over the Germinal Disc of the Hen's Ovum", Poult. Sci., vol. 70 (Suppl. 1), p.149 (1992).

Bunch, D., Leyton, L. and Saling, P., "Sperm Interaction with the Zona Pellucida: Role of a Tyrosine Kinase Receptor for ZP3 in Fertilization", Schering Foundation Workshop, vol. 4, pp. 367–381 (1992).

Burkman, L.J., Coddington, C.C., Franken, D.R., Kruger, T.F., Rosenwaks, Z. and Hodgen, G.D., "The hemizona assay (HZA): development of a diagnostic test for the binding of human spermatozoa to the human hemizona pellucida to predict fertilizing potential", Fertil. Steril., vol. 49, pp. 688–697.

Calvete, J.J., Sanz, L., and Töpfer–Petersen, E., "Carbohydrate–Binding Proteins Involved in Gamete Interaction in the Pig," Schering Foundation Workshop, vol. 4, pp. 395–417 (1992).

Davis, A.P., Graham, J.K. and Foote, R.H., "Homospermic Versus Heterospermic Insemination of Zona–Free Hamster Eggs to Assess Fertility of Fluorochrome–Labeled Acrosome–Reacted Bull Spermatozoa", Gamete Res., vol. 17, pp. 343–354 (1987).

Franken, D.R., Acosta, A.A., Kruger, T.F., Lombard, C.J., Oehninger, S. and Hodgen, G.D., "The hemizona assay: its role in identifying male factor infertility in assisted reproduction", Fertil. Steril., vol. 59, pp. 1075–1080 (1993).

Gwatkin, R.B.L. and Williams, D.T., Receptor activity of the hamster and mouse solubilized zona pellucida before and after the zona reaction, J. Reprod. Fertil., vol. 49, pp. 55–59 (1977).

Hawk, H.W., Conley, H.H., Wall, R.J. and Whitaker, R.O., "Fertilization Rates in Superovulating Cows After Deposition of Semen on the Infundibulum, Near the Uterotubal Junction or After Insemination with High Numbers of Sperm", Theriogenology, vol. 29, pp. 1131–1142 (1988).

Howarth, B., "Avian Sperm–Egg Interaction: Perivitelline Layer Possesses Receptor Activity for Spermatozoa", Poult. Sci., vol. 69, pp. 1012–1015 (1990).

(List continued on next page.)

Primary Examiner—Ralph Gitomer
Attorney, Agent, or Firm—Thomas J. Monahan

[57] ABSTRACT

A method for testing the potential fertility of spermatozoa in a sample by contacting an aliquot of the sperm sample onto a protein extracted from native vitelline membranes removed from chicken or turkey eggs to enable quantification of the number of sperm which bind to the protein. Typically, the vitelline membrane protein is coated onto a solid substrate and the protein extract is first prepared by dissecting vitelline membranes (lamina perivitelline plus lamina extravitellina) from either a group of chicken eggs or a group of turkey eggs, rinsing the membranes free of albumin and yolk, and subdividing the membranes into small particles. The resulting protein is heat solubilized, purified with centrifugation and concentrated to yield the protein extract in solution. The extracted protein then is used as a protein substrate for spermatozoa binding, with sequential contacting of the protein extract with the spermatozoa and measuring the amount of sperm-egg binding that takes place. Intact egg membranes may alternatively be used to bind sperm. Correlation between sperm-egg binding and fertility of the spermatozoa in the sample is direct and linear.

12 Claims, 3 Drawing Sheets

OTHER PUBLICATIONS

Howarth, B., "Carbohydrate Involvement in Sperm–Egg Interaction in the Chicken", *J. Receptor Res.*, vol. 12, pp. 255–265 (1992).

Kido, S. and Doi, Y., "Separation and Properties of the Inner and Outer Layers of the Vitelline Membrane of Hen's Eggs", *Poult. Sci.*, vol. 67, pp. 476–486 (1988).

Saling, P.M., "Mammalian sperm interactions with extracellular matrices of the egg", *Oxford Rev. Reprod. Biol.*, vol. 11, pp. 339–388 (1989).

Wassarman, P.M., "Regulation of Mammalian Fertilization by Gamete Adhesion Molecules", *Schering Foundation Workshop*, vol. 4, pp. 345–366 (1992c).

Wishart, G.J., "Regulation of the length of the fertile period in the domestic fowl by numbers of oviducal spermatozoa, as reflected by those trapped in laid eggs", *J. Reprod. Fertil.*, vol. 80, pp. 493–498 (1987).

Wishart, G.J., Staines, H.J. and Steele, M.G., "A Method for Predicting Impending Infertility in Naturally–Mated Chickens and Demonstration of Gross Variation in Sperm Transfer Efficiency", *XIX World Poult. Congr.*, vol. 1, pp. 631–634 (1992).

J. J. Phillips et al., "Cryopreservation of Rooster Sperm using Methyl Cellulose", *Poultry Science*, vol. 75 (1996), pp. 915–923.

K.M. Silverberg et al., "The Modified D–Mannose In Vitro Binding Assay (MBA) Predicts Fertilization In Vitro" (Abstract), *Fertility & Sterility*, vol. 60, Suppl. 1, p. 556 (1993).

Wishart, G.J., "Physiological Changes in Fowl and Turkey Spermatozoa During In Vitro Storage", *British Poultry Science*, vol. 30, pp. 443–454 (1989).

FIG. 3 HORSE SPERM BINDING TEST

FIG. 4 MOUSE SPERM BINDING TEST

FIG. 5

PROCESS FOR EVALUATING FERTILITY OF SPERMATOZOA SAMPLES

This application is a continuation of copending application Ser. No. 08/234,448 filed on Apr. 28, 1994 now abandoned.

FIELD OF THE INVENTION

The present invention relates to an evaluation process for assessing the fertility of avian and mammalian spermatozoa.

BACKGROUND OF THE INVENTION

Assisted reproductive technologies such as artificial insemination have been practiced commercially with livestock and horses for almost a century, and with poultry, humans and other species for almost a half century. Artificial insemination requires a sample of semen consisting of spermatozoa together with seminal plasma contributed by the epithelial cells of the epididymis and accessory organs. In addition to water, seminal plasma contains numerous proteins and glycoproteins, phospholipids, lipids, carbohydrates and ions.

It was recognized early on that a sample of semen contains a heterogeneous population of sperm, with some having—and others lacking—fertilizing potential. Thus, potential fertility differs from sample to sample for a given male, and differs greatly among different males of a species. Prediction of potential fertility is a recurring question in human medicine and in research on sperm from animals of economic importance. A potential effect on fertility is intrinsic to any attempt to improve methods for preservation of sperm, or in efforts to solve the many unanswered mysteries of sperm biology. Unfortunately, valid assessment of fertility of an individual male has heretofore been expensive for species such as cattle and chickens, impractical and expensive for horses, and impossible for humans.

For many years it has been recognized that potential fertility of a given seminal sample is difficult to measure accurately. Numerous approaches have been used, but no single method tests all of the attributes of sperm function that contribute to fertility. Tests evaluating percentage of motile sperm, motion characteristics of sperm, or exposed carbohydrates or membrane integrity are somewhat useful, but are not reliably predictive. Motile sperm with a normal morphology are more likely to be fertile than immotile sperm or sperm with a bizarre shape or structure. Nevertheless, neither subjective nor objective measurements of sperm motility or morphology have proven to be highly predictive of potential fertility.

A review of the binding mechanism between spermatozoa and eggs is instructive in this context. The initial event in the fertilization process is the binding of one or more sperm to the egg investments. In mammals, a spermatozoon is considered to bind to the oocyte through a series of egg-binding proteins, collectively called ligands, located on the surface of the spermatozoon which interact with appropriate members of a series of sperm receptors located on the investments of the oocyte, namely, the zona pellucida and oocyte plasma membrane. This terminology for location of binding proteins on the sperm and receptors on the egg is most logical, is traditional with invertebrates and applicable to mammals, and will be used hereafter with reference to both mammals and birds.

Egg-binding proteins of mammalian sperm generally are considered to be transmembrane proteins or glycoproteins, possibly with enzymatic activity, with an extracellular domain that interacts with a specific sperm receptor. The consensus scenario which has evolved is one of sequential binding: first a loose binding to the zona pellucida via one or more molecule(s) located on the sperm plasma membrane; then a tight binding of the sperm to the zona pellucida via molecule(s) located on the plasma membrane and/or the acrosomal membrane; followed by tight binding of the sperm to the oocyte plasma membrane followed by fusion of the sperm and egg plasma membranes and entrance of the entire spermatozoon into the oocyte. Thus, species-specific adhesion between sperm and eggs is attributable to complexes formed between egg-binding proteins on sperm and complementary sperm receptors on eggs. At least one species non-specific egg-binding protein also must be located on the sperm surface.

Eggs also have receptors for sperm ligands. In mammals, the plasma membrane of the egg is overlain by the zona pellucida, an acellular coating formed around the oocyte while it is still within the ovarian follicle. Depending on the species, the zona pellucida may limit access of supernumerary sperm to the plasma membrane. In common mammals, fertilization apparently follows a similar process which features a pivotal role for the highly conserved zona pellucida, comprised of several glycoproteins in the mouse termed $ZP_1$, $ZP_2$, and $ZP_3$. A loose non-specific binding of a spermatozoon to the zona pellucida is followed by strong attachment of sperm ligands to receptors on $ZP_3$, initiation of the acrosome reaction and conversion of proacrosin to acrosin (a serine protease), binding to $ZP_2$, enzymatic digestion of a channel for that spermatozoon through the zona pellucida and passage of the spermatozoon into the underlying perivitelline space, after which other sperm ligands bind to receptors on the oocyte plasma membrane. It is unclear if sperm motility is requisite for these binding responses, but motility certainly is necessary for penetration of the zona pellucida. Obligatory steps include (1) initial loose binding of a spermatozoon to the zona pellucida and (2) subsequent tight binding by receptors on $ZP_3$. Given the pivotal role in fertilization of penetration of sperm through the zona pellucida, it is not surprising that the number of sperm trapped in the zona (termed accessory sperm) is related to the fertilization status of the oocyte therein; the more sperm, the greater the probability that fertilization occurred.

In birds, the maternal gamete and yolk of an ovulated egg is encircled by a multilayered egg membrane (vitelline membrane), comprised of a distinct inner lamina perivitelline and an outer mesh-like lamina extravitellina. After passage of the egg from the infundibulum into the magnum of the oviduct, a series of albumin coats are added followed by components associated with the shell. Avian sperm normally can penetrate the lamina extravitellina and bind to the lamina perivitelline, steps essential for fertilization, only during the approximately 15 minutes which elapse between ovulation and deposition of the initial albumin coat. Accessory sperm can be found on or within the egg membrane of a fertilized egg. Little research has been done on the molecular nature of the egg membranes or sperm-egg binding in chickens.

However, it is known that the lamina perivitelline is composed primarily of 3 glycoproteins while the lamina extravitellina is a mixture of other components.

There have been to date countless approaches to evaluate sperm quality, and correlation of test results with known fertility data is not the same as accurately predicting fertility in an unknown sample—which has not been done to date. Accordingly, a need remains for a simple and accurate test to assess the fertilization potential of spermatozoa in a single sample from an individual mammalian or avian organism. Such a test is useful both in human health care and commercial animal breeding.

SUMMARY OF THE INVENTION

The present invention is a method for testing the potential fertilizing capability of spermatozoa by placing a suspension of these spermatozoa onto a protein extracted from native vitelline membranes removed from chicken or turkey eggs, with the protein usually having first been coated onto a solid substrate, to enable quantification of the number of sperm which bind to the protein. Typically, the vitelline membrane protein extract is prepared by dissecting vitelline membranes (lamina perivitelline plus lamina extravitellina) from either a group of chicken eggs or a group of turkey eggs, rinsing the membranes free of albumin and yolk and subdividing the membranes into small particles mechanically by ultrasonic energy shearing. The resultant divided protein is solubilized, purified, centrifuged and concentrated to yield the protein extract in solution. The extracted protein then is used as a protein substrate for spermatozoa binding, with sequential contacting of the protein extract with the spermatozoa and measuring of the amount of sperm-egg binding that takes place. Alternatively, the washed egg membrane, before shearing and solubilization, can be laid on a solid substrate to provide the binding surface. Correlation between sperm-egg binding and fertilizing potential of the spermatozoa is direct and linear.

DETAILED DESCRIPTION OF THE INVENTION

The present invention is a method for testing the fertility of a sample of spermatozoa by contacting aliquots of the sample onto a protein extracted from native vitelline membranes removed from chicken or turkey eggs, or onto the vitelline membranes themselves, to enable quantification of the number of sperm which bind to the protein. Typically, when the protein extract method is used, the vitelline membrane protein extract is prepared by dissecting vitelline membranes (lamina perivitelline plus lamina extravitellina) from either a group of chicken eggs or a group of turkey eggs, rinsing the membranes free of albumin and yolk and subdividing the membranes into small particles by applying mechanical ultrasonic shearing. The resultant protein then is solubilized in buffer with heat, purified with centrifugation and concentrated (for example with a 10 kDa cutoff ultrafiltration membrane) to yield the protein extract in buffered solution. The extracted protein then is used as a protein substrate for spermatozoa binding, with sequential contacting of the protein extract with the spermatozoa and determining the number of sperm bound because of sperm-egg binding reactions. The determination can be visual counting by microscopy, or an automated equivalent using commercially available microscopic image analysis software, or the use of commercially available microwell plate readers quantifying absorbance or fluorescence or stained spermatozoa. Correlation between sperm-egg binding and fertility (fertilizing ability) of the spermatozoa in the sample is direct and linear.

More particularly, the present method is conducted as follows.

The vitelline membranes are dissected from chicken or turkey eggs (one or the other but not both, either fresh unfertilized or stored up to 6 months at 2°–5° C.) and rinsed free of albumin and yolk by repeated immersion and shaking in repeated washes of cleansing buffer. A typical cleansing buffer contains 50 mM sodium phosphate and 145 mM sodium chloride, pH 7.2, but equivalent buffers can be substituted. In general, throughout this specification any buffer may be substituted for any other buffer as long as the buffer is generally acceptable for suspending or washing biological materials, according to ordinary skill in the art. The washed vitelline membranes are either used immediately or are stored in cleansing buffer at 2°–5° C. for up to several days before use. The membranes then are subdivided into small particles by applying mechanical or ultrasound energy. The resultant material is solubilized, purified with centrifugation and concentrated to yield an egg membrane protein extract in solution.

By "protein," in the context of the present invention and the protein found in the egg membrane which is capable of binding spermatozoa, applicant means any biomolecule containing an amino acid chain or peptide moiety including but not limited to lipoproteins and glycoproteins. In other words, for the purpose of this invention a broad definition of protein has been adopted and is intended.

The suspensions are pooled and the total volume brought to 6 mL/membrane with additional buffer. The suspensions are heated in a closed vessel at 73° C. for 20 minutes to solubilize the protein, cooled to 4° C., and centrifuged at 27,000×G at 4° C. for 15 minutes. The supernatant protein solution is aspirated and concentrated using a 10-kDa cutoff ultrafiltration membrane to provide a solution containing approximately 2.5 mg/mL protein. Other methods to extract the protein are possible, and the active protein molecule(s) can be purified by any method. The solution can be used immediately to coat slides or microwell plate wells, or stored at −20° C. for at least 3 months.

Subsequently, the cavities in a microwell plate are coated with the protein extract from vitelline membrane (a concentration of 2.5 mg/mL protein in 20 mM Tris-HCl buffer, pH 8.0, is typical of one series of extracts used) to obtain a thin, uniform layer. With purer membrane extracts, less material need be coated to the substrate. The protein should be rapidly dried, using low heat applied under vacuum, although the protein can be air dried. After the coating is dry, the coated plate can be used immediately or stored in a humidified cold environment.

In order to use the microscope slide prepared as above, a template is laid over a clean intact egg membrane placed on a microscope slide. The template is simply a generally flat construct with holes in it so that upon overlaying the template onto the egg membrane, individual reaction wells result. The template may be made of any material, such as silicone rubber, which does not bind spermatozoa and is nontoxic to sperm. The template can be bonded to the slide with nontoxic adhesive (e.g., UV-catalyzed adhesives known in the art) or clamped in place, and the slide/template combination can be used immediately or stored under humidified cold conditions.

Figure 1:
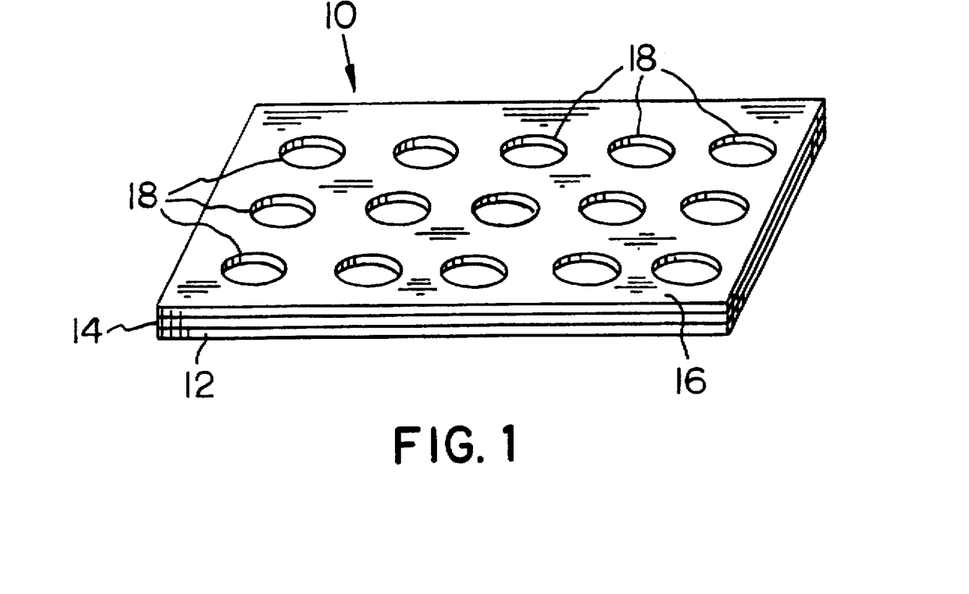
FIG. 1 is a perspective view of a microscope slide, coated with an intact membrane according to the invention, covered by a template with holes to form wells in which to assay sperm fertility.
Figure 2:
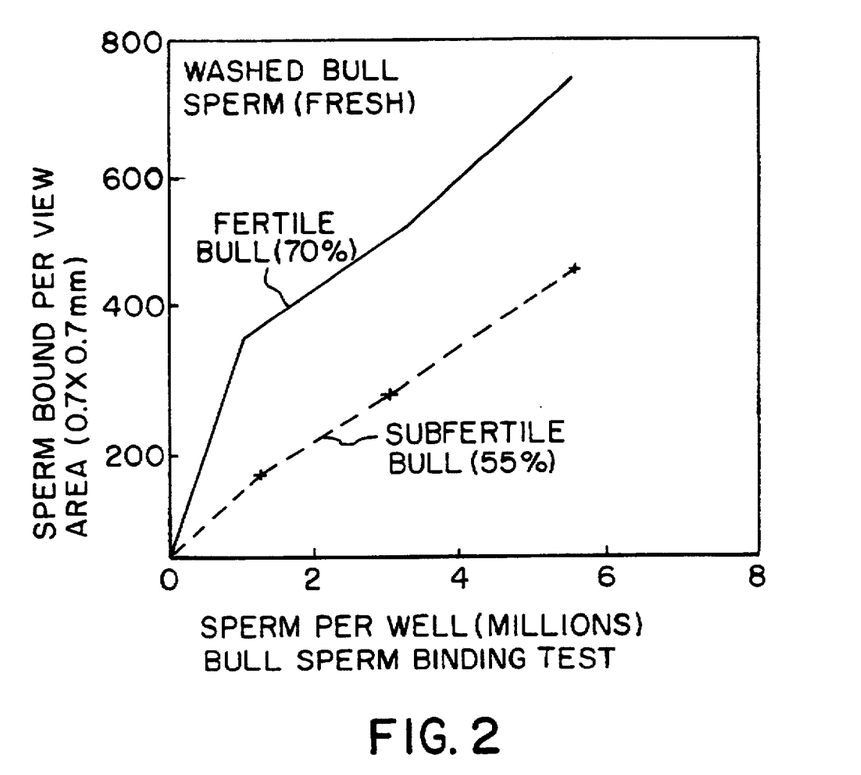
FIG. 2 is a graph showing the results of a bull sperm binding test described in Example 10, below.

Referring now to FIG. 1, the combined prepared egg membrane, microscope slide and template are shown as the well device 10, having the microscope slide 12 having an egg membrane 14 (or protein coating) thereon, with the microscope slide 12 being bonded with a peripheral layer of bonding agent (not visible) to a template 16 having holes 18 therein. The invention embraces any well devices having the present egg membrane or protein coating deposited therein, so FIG. 1 is merely exemplary.

For use, the wells in the device are rinsed with buffer and used to assay for sperm utility, as follows.

Spermatozoa in suspension with autologous seminal plasma and added buffer, or preliminarily washed free of seminal plasma, are added dropwise to the wells formed by the template and the microscope slide. Incubation is conducted by leaving the sperm in the well for about 1-3 hours at 37° C. in a humidity chamber. After incubation, the sperm suspension is decanted, and each well is rinsed with buffer, with agitation, for 3 minutes. A method for consistent washing of membranes is crucial for reproducible results.

After rinsing, the bound sperm are stained with 4,6-diamidino-2phenylindole (DAP; 1 µg/mL in PBS buffer) and are examined under a fluorescent microscope. The number of sperm bound per unit area of membrane is then counted. The correlation between number of bound sperm counted and fertility of the sample is direct and linear.

The present method can be conducted with washed intact chicken egg or turkey egg membranes, if desired, rather than preparing the membranes in solution and coating a solid substrate. The intact membranes are more difficult to handle than the protein extract, however, because of their fragility, the difficulty of arranging them without bubbles or wrinkles on a solid support, and the more difficult viewing of their wrinkled surface under microscopy. Despite these disadvantages, however, the use of egg membranes per se has utility, and thus forms a part of the present invention. In fact, inasmuch as the following examples are presented in the order they were conducted as the present invention was developed, the earliest examples recite the use of intact egg membranes.

The following examples are illustrative, and are not intended to limit the invention in any way.

EXAMPLE 1

Vitelline membranes (lamina perivitelline plus lamina extravitellina) were dissected from chicken eggs (fresh unfertilized chicken eggs were used but eggs stored up to 6 months at 2°-5° C. could have been substituted), and rinsed free of albumin and yolk by repeated immersion and shaking in a series of beakers containing swirling cleansing buffer (50 mM sodium phosphate, 145 mM sodium chloride; pH 7.2). The washed vitelline membrane was used immediately, although it could have been stored in cleansing buffer at 2°-5° C. for several days before use. The membrane was not allowed to dry out between removal from the egg and use in the assay.

Washed vitelline membranes from turkey eggs also were prepared in the same manner.

To prepare the assay device, a microscope slide was cleaned and dried for use. A template of silicone rubber that contained a series of holes of uniform size (3-10 mm across) was prepared. Silicone rubber was selected because it is not toxic to sperm, it can be readily cut to contain holes of a uniform and standard size, and can form a seal when placed between adjacent surfaces. The template was coated with a nonstick substance (Fisher Brand Dricote, known in the art, was used) to prevent adherence of cells to the template materials during the assay.

A segment of vitelline membrane was laid over a 24×24–40 mm coverslip, taking care to avoid folds or tears. Immediately the silicone-coated template was laid over the membrane, so that the wells in the template were superimposed over the vitelline membrane. The template was clamped over the membrane using plastic clamps, and the holes in the template formed wells for dropwise addition of sperm suspension or control admixtures.

The wells in the template were rinsed with buffer and shaken to dislodge the excess. Then, a measured aliquot of sperm suspension was placed into each well. The sperm suspension included spermatozoa, buffer and autologous seminal plasma. The sperm were left in the well for 1-3 hours at 37° C. in a humidity chamber. After incubation, the sperm suspension was decanted, and each well was rinsed with buffer, with agitation, for 3 minutes. A method for consistent washing of membranes was crucial for reproducible results.

After rinsing, the bound sperm were stained with 4,6-diamidino-2phenylindole (DAP;1 µg/mL in PBS buffer) and were examined under a fluorescent microscope. The number of sperm bound per unit area of membrane was counted. Appropriate controls were used in parallel wells, and included: sperm rendered immotile, sperm damaged to remove ligands binding to the membrane, or sperm coincubation with an excess of molecules known to block or enhance the binding reaction.

Initial validation of the general assay procedure used slides and templates in which each well held about 20 µL. To establish that the number of sperm bound was a function of the number of motile sperm in the well, a dose response test was conducted; wells contained 0.15 to 10×10$^6$ fresh sperm (about 80% motile) or 10 ×10$^6$ killed sperm (flash frozen to −196° C 3X). After 3 hours of incubation, unbound sperm were washed away, bound cells were stained, and sperm in a 0.5-mm$^2$ area were counted at 156× magnification. A dose response curve was obtained.

EXAMPLE 2

Example 1 was repeated except both fertilized and non-fertilized eggs were used, separately, to compare and to evaluate the ability of sperm to bind to membranes recovered from unfertilized or fertilized eggs of similar freshness. It was found that more motile sperm were bound by unfertilized eggs than fertilized eggs, and that the discrimination between live and killed sperm also was greater. This established that vitelline membranes to be used in the present method are preferably taken from unfertilized eggs.

EXAMPLE 3

In order to ascertain the relationship of the in vitro results to fertility of the same samples when used for artificial insemination, the following test was conducted. One volume of rooster sperm was extended with three volumes Minnesota-A buffer containing 12% glycerol, was frozen to −196° C., and was carefully thawed. Glycerol was diluted by serial addition of Minnesota-A buffer and sperm were recovered by centrifugation. The sperm pellet was resuspended in Minnesota-A buffer (standard cryopreservation procedure).

Freshly collected sperm (no cryopreservation) were diluted in Minnesota-A buffer to serve as a control preparation. Aliquots of 100×10$^6$ sperm representing each of the 2 treatments were tested using the assay described herein. Fertility of the sperm suspensions also were established using 17–19 hens/group. The results illustrate that the ranking of the 2 samples obtained with the egg membrane binding assay was far more diagnostic of fertilizing capability than either percentage of motile sperm or percentage of sperm with an intact plasma membrane see Table 1, below.

TABLE 1

Comparison of laboratory and fertility assays of fresh and cryopreserved rooster sperm

| Treatment | Percent Motile Sperm | Percent Intact Sperm | Relative Sperm-Egg Binding | Mean Fertility (percent) |
|---|---|---|---|---|
| Diluted sperm (Control—No Cryopreservation) | 95 | 100 | 100 | 86 |
| Standard Cryopreservation | 70 | 73 | 18 | 34 |

EXAMPLE 4

In order to determine any changes in fertilizing potential of rooster sperm after storage of the sperm at 4° C. for 0, 24 or 48 hours the following test was conducted. After storage of rooster sperm for the above-stated periods of time, aliquots of sperm were evaluated for motility and resistance to hypoosmotic shock (both by methods known in the art), and in vitro binding to an egg membrane as described in Example 1. Other aliquots were used to inseminate groups of 60, 60 and 14 hens with 75, 75 or 130×10$^6$ sperm for sperm stored at 0, 24 or 48 hours, respectively; 356, 350 and 72 eggs were evaluated. Actual egg fertilizations, extent of egg-membrane binding of sperm and the degree of sperm plasma membrane damage were all determined, under microscopy where necessary, and the results appear in Table 2, below.

TABLE 2

Comparison of rooster spermatozoal characteristics in laboratory assays and fertility tests

| Treatment | Motility % motile ((%) D/min.)) | Motility 1/velocity t$^{1/2}$ | % Intact Sperm Plasma Membranes | Fertility (%) | Relative Sperm-Egg Binding Assay |
|---|---|---|---|---|---|
| Zero Time (No Storage) | 62 | 164 | 91 | 34 | 100 |
| Stored at 6° C. for 24 Hours | 30 | 97 | 93 | 14 | 60 |
| Stored at 6° C. for 48 Hours | 31 | 90 | 88 | 4 | 30 |

Few of the sperm had a damaged plasma membrane regardless of storage interval (all values <12% damaged), and based on sperm motility the quality of samples stored for 24 or 48 hours were similar, but were inferior to those examined at 0 hours before storage (approximately 50% reduction). The egg membrane binding assay was the only in vitro sperm quality test which detected a difference in potential fertility between sperm stored 24 hours and sperm stored 48 hours: fertility of samples decreased between 0 and 24 hours and further between 24 and 48 hours. The inventive assay is thus illustrated to have utility in predicting fertility of both fresh and stored sperm specimens, and for stored specimens can even detect loss of fertility over time.

EXAMPLE 5

The following test was conducted to determine the efficacy of the present technique in evaluating the fertility of turkey spermatozoa.

Membranes from chicken hen eggs were prepared for use with fresh (with a high percentage of motile sperm), killed (by cooling to −196° C.; no motile sperm), or 24 hours stored turkey sperm. The assay was performed according to Example 1; each well contained 2.5×10$^6$ turkey sperm in 20 µL volume. Results were determined in accordance with Example 1 and yielded the following values: Fresh spermatozoa (expressed in terms of a normalized value of 100%) bound to the egg membranes; approximately 30% of that amount bound when stored spermatozoa were tested for binding to the egg membranes; and only about 3% of the killed spermatozoa bound to the egg membranes. It was thus readily apparent that fresh turkey sperm became bound to the egg membrane, and that such binding was greatly reduced for motile sperm tested after 24 hours storage. Further, fresh and stored sperm were both bound in far greater numbers than killed sperm. The same numeric results were obtained when egg membranes from turkey hens were used in substitution for the chicken eggs, in a parallel test.

EXAMPLE 6

Preparations containing rooster, bull and ram sperm were incubated with hen's egg membrane as described in Example 1 and then were examined under electron microscopy. Rooster sperm showed close orientation to the outer portion of the perivitelline membrane, whereas bull and ram spermatozoa did not enter the membrane to the same degree, but rather were embedded in an unknown material adhering to the outer membrane of the hen's egg with sperm heads lined up in parallel. This trial illustrated that spermatozoa from different species bind to egg membrane when subjected to the present assay, and also that the nature of the binding may differ by species.

EXAMPLE 7

We compared ability of an assay using the present protein extract and native egg membrane for their abilities to discriminate between samples of fresh rooster sperm (samples contained a high percentage of motile sperm), intentionally killed sperm (rapidly frozen to −196° C. without cryoprotectant—no motile sperm), and sperm cryopreserved by two different conventional procedures.

The protein extract was prepared as follows. The vitelline membranes of chicken eggs were dissected and rinsed free of albumin and yolk by repeated immersion and shaking in repeated washes of 50 mM sodium phosphate and 145 mM sodium chloride, pH 7.2. The washed vitelline membranes were then subdivided into small particles by applying ultrasound energy. The resultant protein was solubilized by heating in a closed vessel at 73° C. for 20 minutes, followed by cooling to 4° C., and centrifuging at 27,000×G at 4° C. for 15 minutes. The supernatant protein solution was aspirated and concentrated using a 10-kDa cutoff ultrafiltration membrane to provide a solution containing approximately 2.5 mg/mL protein. The solution was applied (110 µL/well) to a microwell plate and evaporated under a vacuum and heat (60° C.).

Spermatozoa in suspension with buffer and traces of autologous seminal plasma were added dropwise to the wells formed by the template and the microscope slide. Incubation was conducted by leaving the sperm in the well for about 2.5 hours at 37° C. in a humidity chamber. After incubation, the sperm suspensions were decanted, and each well was rinsed with buffer, with agitation, for 3 minutes. After rinsing, the bound sperm were stained with 4,6-diamidino-2-phenylindole (DAP1; 1 µg/mL in PBS buffer) and were examined under a fluorescent microscope. The number of sperm bound per unit area of membrane was counted.

Direct comparison revealed that equivalent results were obtained with either assay, as shown in Table 3.

TABLE 3

Percent cells bound by egg membrane vs. protein extract

| Sperm Type | Intact Membrane | Protein Extract |
| --- | --- | --- |
| Live Sperm | 100 | 100 |
| Cryopreserved Sperm | 70 | 78 |
| Cryopreserved Sperm (Alt. Technique) | 30 | 33 |
| Dead Sperm | 9 | 7 |

EXAMPLE 8

Example 7 was repeated except proteins extracted from chicken eggs versus turkey eggs were compared. Both fresh chicken and turkey sperm bound in similar proportions to protein extracts taken from either chicken or turkey eggs, whereas <5% of the killed sperm bound to either extract. Frozen thawed sperm from either species bound to both membranes, although the percentages were intermediate between values for fresh and killed sperm. There was a tendency for a slightly greater percentage of the cryopreserved rooster sperm to bind to turkey membrane preparations than to those from chicken eggs. These results substantiate that capability of this general assay to provide data in which the percentage of sperm bound may be predictive of fertility does not require use of native vitelline membranes, but can be performed using protein extracts and, by logical extension, pure native protein(s) or the appropriate protein produced by recombinant technology and in vitro or in vivo expression of appropriate constructs.

EXAMPLE 9

We took a microtiter plate and placed 110 µL of the protein extracted from vitelline membrane (a concentration of 2.5 mg/mL protein in 20 mM Tris-HCl buffer, pH 8.0) preheated to 37° C. into each well and dried the protein under low heat and vacuum. Then we placed 100 µL of incubation buffer in each well together with an appropriate number of test sperm and incubated the wells for 2.5–3.0 hours at 37° C. in a humidity chamber. After incubation, we decanted the contents of all wells and rinsed out each well repeatedly with excess incubation buffer. We fixed the cells to the membrane by exposure to a mixture of 3 parts ethanol and one part acetic acid and then stained the sperm with 4,6-diamidino-2-phenylindole (1 µg/mL in PBS buffer). The number of sperm bound per unit area was quantified by counting using a fluorescence microscope. Data analysis was conducted as described in the foregoing examples.

For example, when we evaluated ability of these data to discriminate between samples of rooster spermatozoa representing fresh semen from unique males, we were able to show that samples differing in capability to bind to the egg membrane are likely to differ in fertilizing capability. Ten sperm samples were tested for binding individually, and as a pooled sample containing equal parts of all samples. Whereas the pooled sample gave a uniform cell binding percentage of about 69%, individual samples gave the respective results of 68%,58%,49%,34%,95%,64%,17%, 78%, 67% and 22%.

EXAMPLE 10

Semen was available from two bulls known to differ in fertility, despite similarity in the percentage of motile and morphologically normal sperm in their semen. Aliquots of fresh, unprocessed semen were diluted, evaluated for percent motile sperm and subaliquots containing 0 to $7 \times 10^6$ sperm were placed into wells in a prepared microtiter plate prepared according to Example 9. Approximately linear dose-response curves were obtained for each sample, and the slopes of the curves were different (see FIG. 4). Few killed sperm bound to the assay plate. These data demonstrated that the present method is a meaningful fertility assay.

EXAMPLE 11

Figure 3:
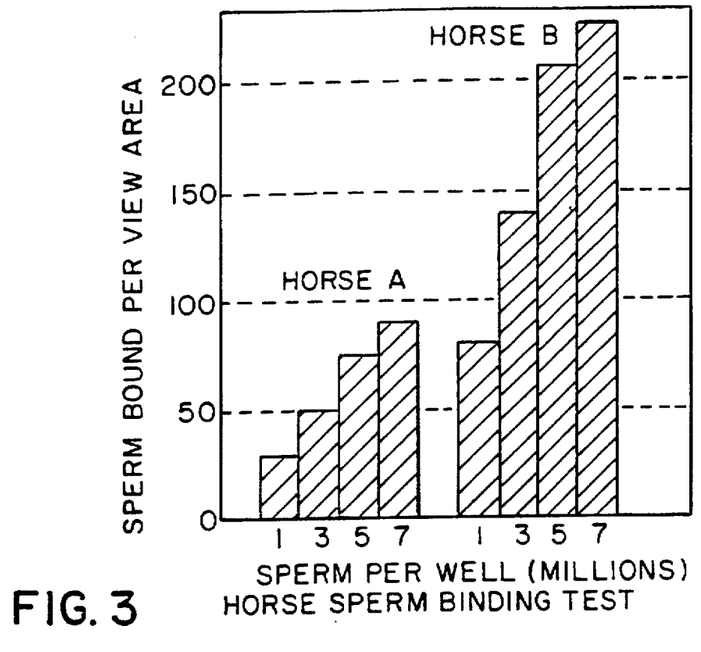
FIG. 3 is a bar graph showing the results of a horse sperm binding test described in Example 11, below.

Frozen semen was available from two stallions. Aliquots of these cryopreserved semen samples were thawed and diluted with TALP buffer. Sperm concentration was determined by cytometer count. Subaliquots containing 0 to $9 \times 10^6$ sperm were placed into wells in a microtiter plate prepared according to Example 9. Approximately linear dose-response curves were obtained for each sample (FIG. 3).

EXAMPLE 12

Figure 4:
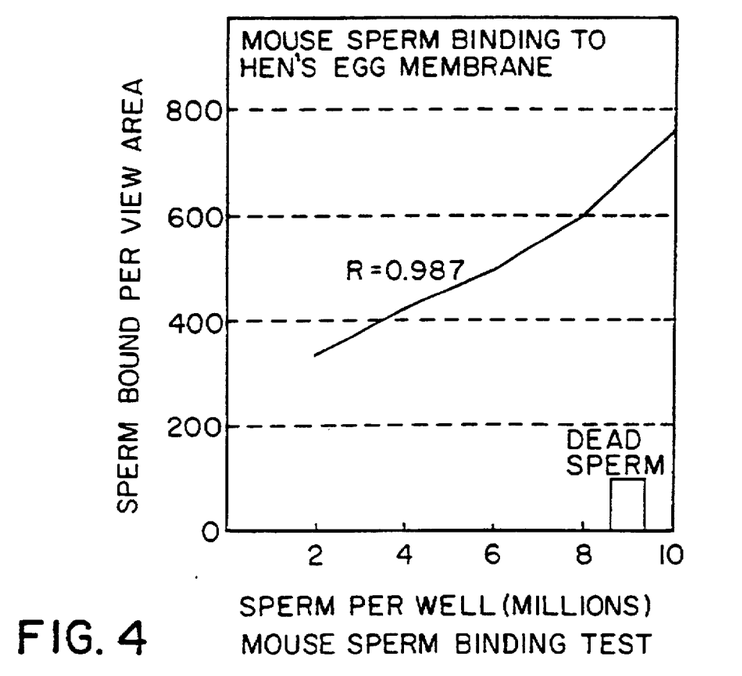
FIG. 4 is a graph showing the results of a mouse sperm binding test described in Example 12, below.

Sperm isolated from the cauda epididymis of mice were collected into TALP buffer, the sperm were enumerated by cytometer count, and aliquots of $1-10 \times 10^6$ sperm were placed into wells in a prepared microwell plate according to Example 9. An approximate linear dose-response curve was obtained (FIG. 4).

EXAMPLE 13

Figure 5:
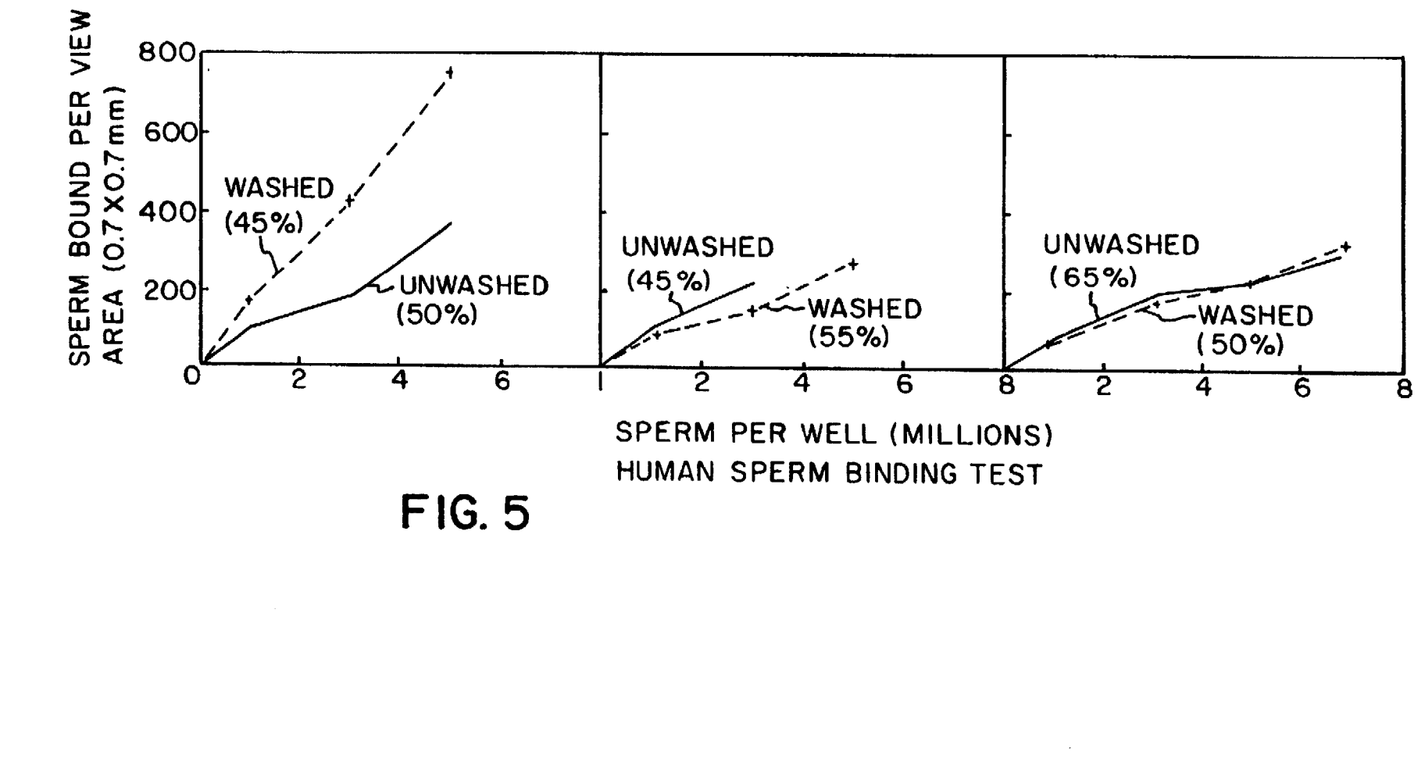
FIG. 5 is a set of three graphs showing the results of human sperm binding tests described in Example 13, below.

Three samples of cryopreserved human semen were available, but fertility of the samples was unknown. After thawing, each sample was deglycerolated by stepwise addition of 3 volumes of TALP buffer and divided into two aliquots. One was not treated further (unwashed), while the second was processed by gentle centrifugation (300×G for 10 minutes) and the sperm were resuspended. Percentage of motile sperm in each sample was estimated. Sperm concentration was determined by cytometer and subaliquots containing 0 to $7 \times 10^6$ sperm were placed into wells in a prepared microtiter plate according to Example 9. Approximately linear doseresponse curves were obtained for each sample, and the slopes of the curves were different (FIG. 5). Very few killed sperm, in aliquots rapidly cooled to −196° C. and then thawed, bound to the binding surface. Thus the assay is useful in determining the utility of human sperm.

Although the invention has been described with reference to specific techniques and results above, the invention is only to be claimed insofar as is set forth in the accompanying claims.

We claim:

1. A method for determining a degree of fertility of a sperm sample comprising:
    contacting the sperm sample with vitelline membrane protein, said protein is isolated from a previously laid avian egg;

incubating said sperm and protein for a period of time sufficient for binding to occur;

washing said protein to substantially remove unbound sperm;

determining a number of sperm bound to said protein; and correlating the number of sperm bound to said protein relative to a number of control sperm bound to a substantially identically prepared protein whereas a greater number of sample sperm bound relative to control sperm bound indicates a greater degree of fertility of said sample sperm than said control sperm.

2. The method according to claim 1 wherein the step of contacting sperm with vitelline membrane protein further comprises the steps of selecting either laid chicken eggs or laid turkey eggs, dissecting vitelline membranes from the eggs, washing said vitelline membranes, extracting protein from said vitelline membranes, coating a solid substrate with said protein, forming wells adjacent the protein coating thus formed and contacting said sperm onto said protein coating.

3. The method according to claim 2 wherein said solid substrate is a microscope slide.

4. The method according to claim 2 further comprising quantifying binding of said sperm onto said protein coating by visually examining said wells under microscopy.

5. The method according to claim 2 further comprising quantifying binding of said sperm onto said protein coating by visually examining said wells under fluorescent microscopy.

6. The method according to claim 2 wherein said vitelline membrane protein is divided into small particles and said small particles are then solubilized, whereby proteins of said solubilized small particles can be retained by a 10 kDa filter.

7. The method according to claim 2 wherein the washing is carried out with a cleansing buffer comprising 50 mM sodium phosphate and 145 mM sodium chloride, pH 7.2.

8. The method according to claim 2 wherein said protein is coated onto said solid substrate by dipping, spraying or rolling a solution containing 2.5 mg/mL protein in 20 mM Tris-HCl buffer, pH 8.

9. The method according to claim 2 wherein said wells are formed by overlaying a silicone rubber template atop said protein coating.

10. The method according to claim 1 wherein the step of contacting sperm with vitelline membrane protein further comprises the steps of selecting either laid chicken eggs or laid turkey eggs, dissecting vitelline membranes from the eggs, washing said vitelline membranes, extracting protein from said vitelline membranes, coating at least one preformed well in a solid support with said protein, rinsing said protein with buffer, placing an aliquot of said sperm in contact with said protein, incubating said sperm in contact with said protein at 27°–30° C. for 10–60 minutes, rinsing said protein, and staining and counting any remaining sperm bound to said protein after said rinsing.

11. The method according to claim 1 wherein the step of contacting sperm with vitelline membrane protein further comprises the steps of selecting either laid chicken eggs or laid turkey eggs, dissecting vitelline membranes from the eggs, washing said vitelline membranes with a buffer of pH 7.2 comprising 50 mM sodium phosphate and 145 mM sodium chloride, dividing said vitelline membranes into small particles, heating and cooling and centrifuging and concentrating said particles into a concentrated protein suspension, and coating a solid substrate with said concentrated protein suspension to form a protein coating, forming wells adjacent said protein coating and contacting said sperm onto said protein coating.

12. The method according to claim 2 wherein said wells are formed by overlaying a plastic template atop said protein coating.

* * * * *